(12) United States Patent
Radivojevic

(10) Patent No.: US 12,268,520 B2
(45) Date of Patent: Apr. 8, 2025

(54) APPARATUS, METHODS AND COMPUTER PROGRAMS FOR MONITORING A USER'S PULSE

(71) Applicant: Nokia Technologies Oy, Espoo (FI)

(72) Inventor: Zoran Radivojevic, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 272 days.

(21) Appl. No.: 16/623,745

(22) PCT Filed: May 29, 2018

(86) PCT No.: PCT/EP2018/063975
§ 371 (c)(1),
(2) Date: Dec. 17, 2019

(87) PCT Pub. No.: WO2019/001874
PCT Pub. Date: Jan. 3, 2019

(65) Prior Publication Data
US 2020/0170566 A1    Jun. 4, 2020

(30) Foreign Application Priority Data

Jun. 30, 2017   (EP) .................................... 17179215

(51) Int. Cl.
*A61B 5/02*   (2006.01)
*A61B 5/00*   (2006.01)
(Continued)

(52) U.S. Cl.
CPC .......... *A61B 5/486* (2013.01); *A61B 5/02438* (2013.01); *A61B 5/02444* (2013.01);
(Continued)

(58) Field of Classification Search
None
See application file for complete search history.

(56) References Cited

U.S. PATENT DOCUMENTS

2005/0070809 A1*  3/2005  Acres ................. A61B 5/02438
                                                   600/508
2008/0300470 A1* 12/2008  Gerber .................. A61B 5/202
                                                   600/301
(Continued)

FOREIGN PATENT DOCUMENTS

WO    2016/123129 A1    8/2016

OTHER PUBLICATIONS

Extended European Search Report received for corresponding European Patent Application No. 17179215.3, dated Dec. 21, 2017, 8 pages.

(Continued)

*Primary Examiner* — Aurelie H Tu
(74) *Attorney, Agent, or Firm* — McCarter & English LLP

(57) ABSTRACT

Methods and Computer Programs for Monitoring a User's Pulse An apparatus, method and computer program, the apparatus comprising; a pulse monitoring module; the pulse monitoring module comprising detecting means for detecting a user's pulse and feedback means for providing haptic feedback to the user indicative of the detected pulse; and controlling circuitry arranged to control the pulse monitoring module so that during a first time period the detecting means is arranged to detect a user's pulse and during a second time period the feedback means is arranged to provide haptic feedback indicative of the detected pulse.

17 Claims, 3 Drawing Sheets

Figure 5:
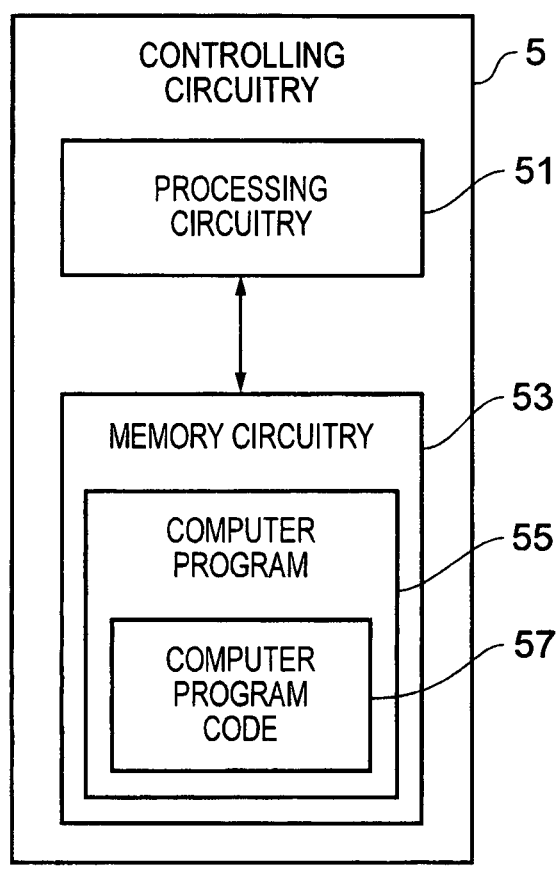

(51) Int. Cl.
  *A61B 5/024* (2006.01)
  *A61B 7/04* (2006.01)
(52) U.S. Cl.
  CPC .......... *A61B 5/6824* (2013.01); *A61B 5/7455* (2013.01); *A61B 7/04* (2013.01)

(56) References Cited

U.S. PATENT DOCUMENTS

| | | |
|---|---|---|
| 2010/0152545 A1 | 6/2010 | Ramsay et al. ............... 600/301 |
| 2014/0077945 A1 | 3/2014 | Amagai |
| 2016/0106360 A1* | 4/2016 | Choi ...................... A61B 5/742 |
| | | 434/247 |
| 2016/0121074 A1* | 5/2016 | Ashby .................. A61B 5/7405 |
| | | 600/27 |
| 2016/0346501 A1* | 12/2016 | Hooper ................ A61B 5/4836 |
| 2016/0366513 A1* | 12/2016 | Zhao .................... A61B 5/6822 |
| 2017/0056725 A1* | 3/2017 | Nakada .................. G16H 40/63 |
| 2017/0135595 A1* | 5/2017 | Baek .................. A61B 5/6832 |
| 2017/0209053 A1* | 7/2017 | Pantelopoulos ... A61B 5/02125 |
| 2017/0224268 A1* | 8/2017 | Altini ................... A61B 5/4356 |
| 2018/0279968 A1* | 10/2018 | Boyd ....................... H04R 1/46 |

OTHER PUBLICATIONS

International Search Report and Written Opinion received for corresponding Patent Cooperation Treaty Application No. PCT/EP2018/063975, dated Jul. 5, 2018, 14 pages.

* cited by examiner

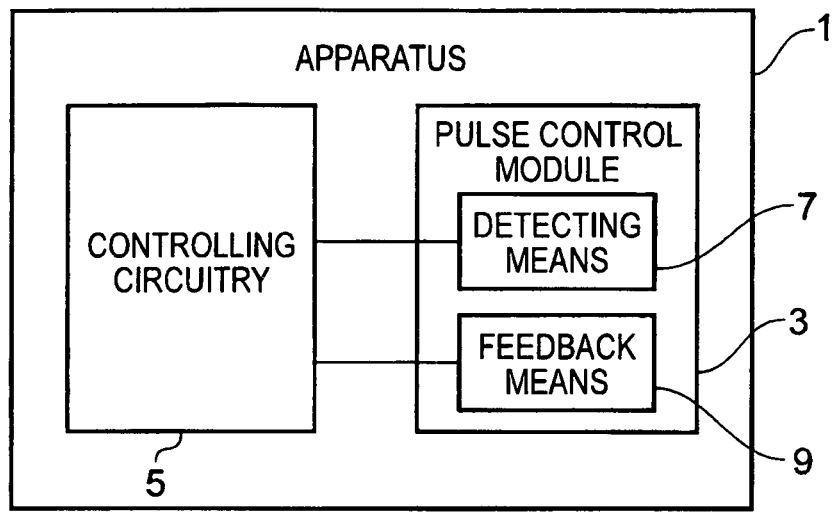
FIG. 1
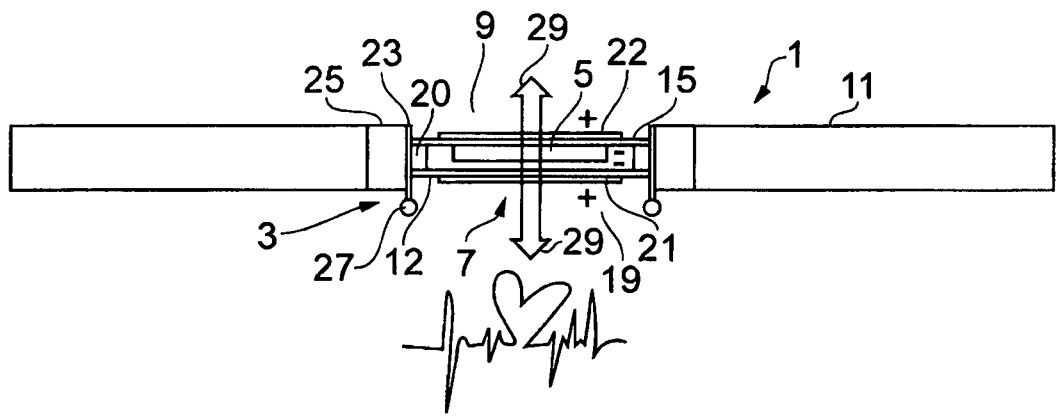
FIG. 2A
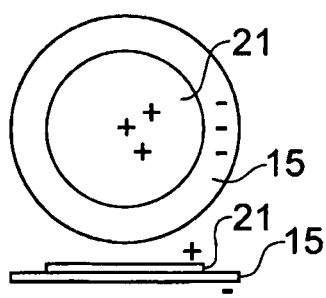
FIG. 2C
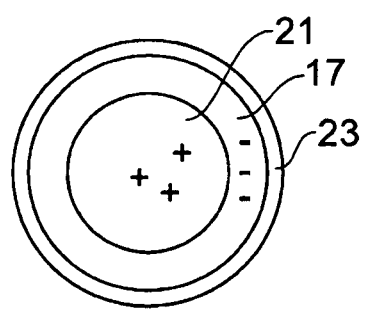
FIG. 2B
FIG. 2D

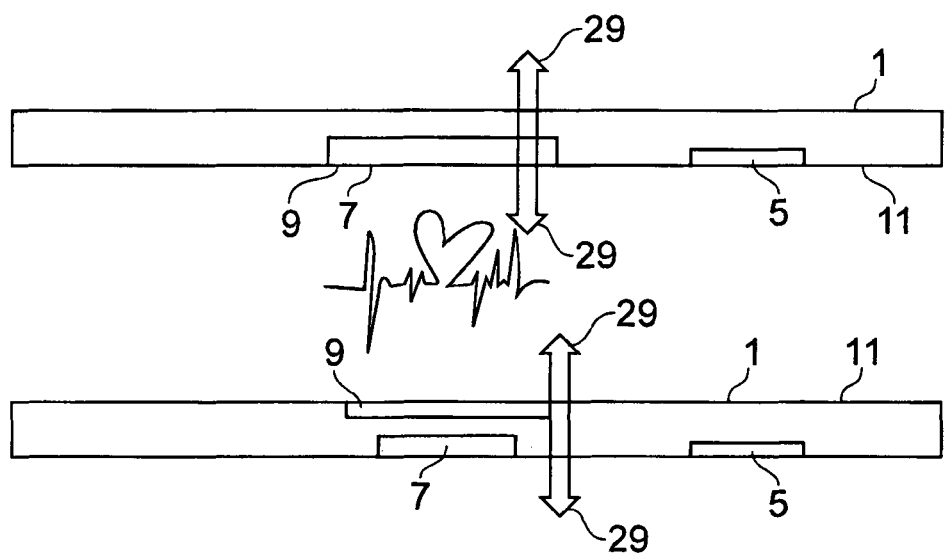
FIG. 3A
FIG. 3B
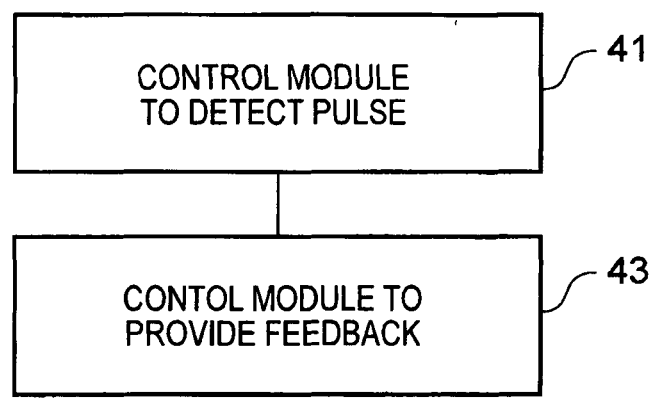
FIG. 4

APPARATUS, METHODS AND COMPUTER PROGRAMS FOR MONITORING A USER'S PULSE

RELATED APPLICATION

This application was originally filed as PCT Application No. PCT/EP2018/063975 filed May 29, 2018 which claims priority benefit from EP patent application Ser. No. 17/179, 215.3 filed Jun. 30, 2017.

TECHNOLOGICAL FIELD

Examples of the disclosure relate to apparatus, methods and computer programs for monitoring a user's pulse. In particular they relate to apparatus, methods and computer programs for monitoring a user's pulse using a wearable device.

BACKGROUND

Apparatus for monitoring a user's pulse are known. Such apparatus may be found in wearable devices such as watches or sensors that can be attached to the user. Such apparatus can be used in a wide range of applications such as health monitoring applications or fitness applications. Once a pulse has been detected it is useful to provide the user with information indicative of the detected pulse.

BRIEF SUMMARY

According to various, but not necessarily all, examples of the disclosure there may be provided an apparatus comprising; controlling circuitry arranged to control a pulse monitoring module, the pulse monitoring module comprising detecting means for detecting a user's pulse and feedback means for providing haptic feedback to the user indicative of the detected pulse, wherein the control circuitry is arranged to control the pulse monitoring module so that during a first time period the detecting means is arranged to detect a user's pulse and during a second time period the feedback means is arranged to provide haptic feedback indicative of the detected pulse.

The second time period may run sequentially to the first time period.

The controlling circuitry may be arranged to control the pulse monitoring module so that the pulse monitoring module alternates between a first time period in which the detecting means is arranged to detect a user's pulse and a second time period in which the feedback means is arranged to provide haptic feedback indicative of the detected pulse.

The feedback means may be arranged to deform a portion of the apparatus so that the deformation of the apparatus can be perceived via a user's sense of touch.

The controlling circuitry may be arranged to control to feedback means to control the frequency of the deformation of the apparatus to correspond to the frequency of the user's detected pulse.

At least one of the detecting means and the feedback means may comprise a piezoelectric transducer. The detecting means and the feedback means may share at least one transducer. The detecting means and the feedback means may share at least one piezoelectric transducer. The pulse monitoring module may comprise a plurality of transducers and at least a portion of the controlling circuitry is positioned between two of the plurality of transducers.

The pulse monitoring module may be provided within a metallic housing. The metallic housing provides a bias electrode for a transducer within the pulse monitoring module.

The apparatus may comprise an elastomeric portion wherein the elastomeric portion is positioned within the apparatus so that when the apparatus is worn by the user the elastomeric portion contacts the user's skin.

The apparatus may comprise a cavity and wherein the cavity has a size and shape arranged to amplify audio pulse signals from a user.

The apparatus may comprise a mass arranged to amplify the haptic feedback of the feedback means.

The apparatus may comprise a coupling means wherein the coupling means enables the apparatus to be worn by a user. The coupling means may comprise a flexible substrate.

According to various, but not necessarily all, examples of the disclosure there may be provided an apparatus comprising; a pulse monitoring module; the pulse monitoring module comprising one or more detectors arranged to detect a user's pulse and one or more actuators arranged to provide haptic feedback to the user indicative of the detected pulse; and controlling circuitry arranged to control the pulse monitoring module so that during a first time period the one or more detectors are arranged to detect a user's pulse and during a second time period the one or more actuators are arranged to provide haptic feedback indicative of the detected pulse.

According to various, but not necessarily all, examples of the disclosure there may be provided a wearable electronic device comprising an apparatus as described above.

According to various, but not necessarily all, examples of the disclosure there may be provided a method comprising: controlling a pulse monitoring module so that, during a first time period, the pulse monitoring module is arranged to detect a user's pulse; and controlling the pulse monitoring module so that, during a second time period, the pulse monitoring module is arranged to provide haptic feedback indicative of the detected pulse.

According to various, but not necessarily all, examples of the disclosure there may be provided an apparatus for performing the method described above.

According to various, but not necessarily all, examples of the disclosure there may be provided a computer program that, when run on a processor, causes controlling a pulse monitoring module so that, during a first time period, the pulse monitoring module is arranged to detect a user's pulse; and controlling the pulse monitoring module so that, during a second time period, the pulse monitoring module is arranged to provide haptic feedback indicative of the detected pulse.

BRIEF DESCRIPTION

For a better understanding of various examples that are useful for understanding the detailed description, reference will now be made by way of example only to the accompanying drawings in which:

FIG. 1 schematically illustrates an example apparatus;

FIGS. 2A to 2D schematically illustrate another example apparatus;

FIGS. 3A and 3B schematically illustrate more example apparatus;

FIG. 4 illustrates an example method which could be used to control the example apparatus; and FIG. 5 illustrates example controlling circuity which may be provided within the example apparatus.

DETAILED DESCRIPTION

The Figures illustrate apparatus 1, methods and controlling circuitry 5 which enable a user's pulse to be monitored and also enable feedback indicative of the user's pulse to be provided to the user. The apparatus 1 comprises a pulse monitoring module 3 which comprises both detecting means 7 and feedback means 9. The detecting means 7 can be arranged to detect the user's pulse and the feedback means 9 can be arranged to provide haptic feedback indicative of the detected pulse. This enables the same module to function as both a detector and a feedback provider. As a single module can perform two functions this reduces the volume of the apparatus 1 which makes it easier for the apparatus 1 to be integrated into a wearable device. Also the apparatus 1 is arranged to provide haptic feedback to the user indicative of their pulse. The haptic feedback may require a smaller cognitive load from the user compared to visual and/or audio feedback.

FIG. 1 schematically illustrates an example apparatus 1 according to examples of the disclosure. The apparatus 1 comprises a pulse monitoring module 3 and controlling circuitry 5.

The pulse monitoring module 3 comprises detecting means 7 for detecting a user's pulse and feedback means 9 for providing haptic feedback to the user indicative of a detected pulse.

The detecting means 7 may comprise any means which may be arranged to detect a pulse of a user and provide an output signal indicative of the detected pulse. The detecting means 7 may comprise one or more detectors. In examples of the disclosure the detecting means 7 may comprise a transducer which may be arranged to detect the audio signal of the user's pulse. The transducer may comprise a piezoelectric transducer which may be arranged to deform when the audio signal of the pulse is detected. The deformation of the piezoelectric transducer may cause an output signal to be provided to the controlling circuitry 5. The frequency of the deformations of the piezoelectric transducer provides an indication of the frequency of the user's pulse.

The detecting means 7 may be positioned within the apparatus 1 so that, in use, the detecting means 7 is positioned adjacent to, or close to, a user's skin. In some examples at least a portion of the detecting means 7 may be provided on the surface of the apparatus 1. The detecting means 7 may be provided on a surface of the apparatus 1 which is positioned adjacent to a user's skin when the apparatus 1 is worn by a user.

The feedback means 9 may comprise any means which may be arranged to provide a haptic feedback to the user. The feedback means 9 may comprise one or more actuators. The haptic feedback may comprise any feedback which can be perceived via the user's sense of touch. In some examples of the disclosure the haptic feedback may comprise a deformation of at least a portion of the apparatus 1. The deformation may comprise the deformation of the feedback means 9. In some examples the deformation may comprise the deformation of other components of the apparatus 1 in addition to the deformation of the feedback means 9. The deformation has a magnitude which is large enough (above one micrometer) for the deformation to be perceived via a user's sense of touch.

In examples of the disclosure the deformation of at least a portion of the apparatus 1 is periodic so that the apparatus 1 is deformed and then returned to an un-deformed state with a frequency controlled by the controlling circuitry 5. The frequency of the deformations may be controlled to be the same as, or provide an indication of, the frequency of the detected pulse of the user.

The feedback means 9 may comprise any means which may be arranged to change shape in response to an input electrical signal. The feedback means 9 may comprise a piezoelectric transducer, electroactive polymer or any other suitable material. In examples where the feedback means 9 comprises a piezoelectric transducer the piezoelectric transducer could be shared with the detecting means 7 so that during a first time period $T_1$ the piezoelectric transducer acts to detect a user's pulse and during a second time period $T_2$ the piezoelectric transducer acts to provide a haptic indication of the frequency of the user's pulse. The first time period $T_1$ and the second time period $T_2$ may have different durations. In some examples the first time period $T_1$ may be longer than the second time period $T_2$. The first time period $T_1$ may be a lot longer than the second time period $T_2$, for example, the second time period $T_2$ could be within a range of 5 to 50 ms while the first time period $T_1$ could be several seconds. Other ranges could be used in other examples of the disclosure.

The feedback means 9 is positioned within the apparatus 1 so that when the feedback means is deformed the deformation can be sensed by the user via their sense of touch. In some examples the feedback means 9, or at least a portion of the feedback means 9 is provided on a surface of the apparatus 1. In some examples the feedback means 9, or at least a portion of the feedback means 9 is provided on a surface of the apparatus 1 which may be positioned adjacent to the user's skin when the apparatus 1 is worn by the user.

In some examples the apparatus 1 may comprise means for amplifying the haptic feedback provided by the feedback means 9. The apparatus 1 may comprise means for amplifying the deformation of the feedback means 9 so that the deformation can be sensed by a user. The means for amplifying the haptic feedback could comprise any suitable means. In some examples it may comprise a mass positioned within the appartaus1 and coupled to the feedback means 9 so as to increase the deformation of the apparatus 1. In some examples the mass could comprise at least some of the controlling circuitry 5. In such examples the mass would be provided internally within the apparatus 1. In other examples the mass could be provided on the outer surface of the apparatus 1. For instance a disc or other component could be provided on the outer surface of the apparatus and coupled to the feedback means 9 to increase the deformation of the feedback means.

The controlling circuitry 5 may comprise any means which may be arranged to control the pulse monitoring module 3. Examples of controlling circuitry 5 are shown in more detail in FIG. 5.

The controlling circuitry 5 is coupled to the detecting means 7 so that a control signal from the controlling circuitry 5 can be provided to the detecting means 7 and an output signal from the detecting means 7 can be provided to the controlling circuitry 5. The control signal may be used to control the time periods at which the detecting means 7 is arranged to detect the user's pulse. The output signal from the detecting means may be used by the controlling circuitry 5 to determine the frequency of the user's pulse.

The controlling circuitry 5 is also coupled to the feedback means 9 so that a control signal from the controlling circuitry 5 can be provided to the feedback means 9. The control signal may be used to control the time periods at which the feedback means 9 is arranged to provide the haptic feedback. The control signal from the controlling circuitry 5 may also be used to control parameters of the haptic feedback. The parameters could comprise the frequency of the deformations, the amplitude of the deformations or any other suitable parameters.

The controlling circuitry 5 may control the frequency of the deformations of the haptic feedback to provide an indication of the frequency of the user's pulse. In some examples the controlling circuitry 5 may control the frequency of the deformations of the haptic feedback so that the haptic feedback has the same frequency as the user's pulse. In other examples the frequency of the deformations could be used to provide information about the user's pulse but does not need to be the same frequency.

In some examples the controlling circuitry 5 could control the amplitude of the deformations of the haptic feedback to provide an indication of the frequency of the user's pulse. In some examples the controlling circuitry 5 may control the amplitude of the deformations so that the amplitude of the deformation is proportional to the frequency of the detected pulse.

In some examples the controlling circuitry 5 could control the amplitude of the deformations of the haptic feedback so that different amplitudes could be used in different applications. For example, if the apparatus 1 is being used by a user currently involved in physical activity the amplitude of the deformations could be increased to make it easier for the haptic feedback to be perceived by the user. Conversely if the apparatus 1 is being used by a user who is currently resting then deformations having a smaller amplitude could be used.

The controlling circuitry 5 is arranged to provide control signals to the pulse control module 3 to cause the pulse control module 3 to sequentially switch between a pulse detecting mode of operation and a feedback mode of operation. The controlling circuitry 5 may cause the pulse control module 3 to switch between the two modes of operation after a predetermined time period. The controlling circuitry 5 may cause the pulse control module 3 to alternate between the two modes of operation FIGS. 2A to 2D schematically illustrate another example apparatus 1 according to an example of the disclosure. FIG. 2A illustrates a cross section of the apparatus 1, FIG. 2C illustrates a side view of a first piezoelectric transducer and FIG. 2D illustrates a plan view of piezoelectric transducer embedded within a metallic housing.

The example apparatus 1 of FIGS. 2A to 2*d* comprises a pulse monitoring module 3 and controlling circuitry 5. The apparatus 1 also comprises coupling means 11.

In the examples of FIGS. 2A to 2D the pulse monitoring module comprises detecting means 7 and feedback means 9 which may be as described above.

In the example of FIGS. 2A to 2D the detecting means 7 comprises a first piezoelectric transducer 21. The piezoelectric transducer 21 has a circular shape and is arranged to expand and contract radially in response to an audio input signal such as the pulse of a user.

The detecting means 7 also comprises a cavity 19. The cavity 19 is positioned adjacent to the piezoelectric transducer 22. The cavity 19 may be an acoustic cavity which may be sized and shaped so as to amplify an audio signal. The cavity 19 may increase the sensitivity of the detecting means 7.

In the example of FIGS. 2A to 2D the feedback means 9 comprises a first piezoelectric transducer 21 and a second piezoelectric transducer 22. The first piezoelectric transducer 21 may also form part of the detecting means 7 so that the feedback means 9 and the detecting means 7 share a common piezoelectric transducer 21. The common piezoelectric transducer 21 is controlled to operate in different modes depending on whether the pulse monitoring module is operating in a detecting mode or a feedback mode. Having the feedback means 9 and the detecting means 7 share a common piezoelectric transducer 21 reduces the number of components required within the apparatus 1. This may enable the size of the apparatus 1 to be reduced which may make the apparatus 1 easier to integrate into a wearable electronic device.

The first piezoelectric transducer 21 and the second piezoelectric transducer 22 may be arranged to change shape in response to an input electric signal. In the examples of FIGS. 2A to 2D both the first piezoelectric transducer 21 and the second piezoelectric transducer 22 have a circular cross section and are arranged to expand and contract radially in response to a control signal from the controlling circuitry 5.

In the examples of FIGS. 2A to 2D the first piezoelectric transducer 21 is provided on a first surface of the apparatus 1 and the second piezoelectric transducer 22 is provided on a second surface of the apparatus 1 so that a space is provided between the two piezoelectric transducers 21, 22. The controlling circuitry 5 may be provided within the space between the two piezoelectric transducers 21, 22. This may reduce the volume required for the apparatus 1 which may make the apparatus 1 easier to integrate into wearable electronic device. This may also enable the controlling circuitry to act as a vibrating mass. This may increase the amplitude of the deformations of the apparatus 1 and/or the force applied to the piezoelectric transducers 21, 22 which may make the deformations easier for a user to sense.

In the example of FIGS. 2A to 2D the pulse monitoring module 3 is provided within a metallic housing 23. The metallic housing 23 may provide means for coupling the first piezoelectric transducer 21 to the second piezoelectric transducer 22. The metallic housing 23 could be made of steel or any other suitable metal.

The metallic housing 23 also has a circular cross section corresponding to the shape of the piezoelectric transducers 21, 22. The piezoelectric transducers 21, 22 may be embedded tightly within the metallic housing 23.

The metallic housing comprises inner fixtures 17, 15 which are coupled to the respective piezoelectric transducers 21, 22. The inner fixtures 17, 15 may provide flexible substrates which supports the piezoelectric transducers 21, 22. The inner fixtures 17, 15 may be arranged to deform as the piezoelectric transducers 21, 22 are deformed.

The inner fixtures 17, 15 may also be arranged to provide a bias electrode for the piezoelectric transducers 21, 22. As the inner fixtures provide both a support and a bias electrode this reduces the number of components within the apparatus 1 which may enable a smaller apparatus 1 to be provided.

The metallic housing 23 also comprises a projection 20. The projection 20 is provided on the inner surface of the metallic housing 23 between the first piezoelectric transducer 21 and the second piezoelectric transducer 22. The projection 20 may be arranged to couple the first piezoelectric transducer 21 and the second piezoelectric transducer 22 together.

The apparatus 1 also comprise an elastomeric portion 27. The elastomeric portion 27 is provided on an end of the metallic housing 23 so that in use the elastomeric portion 27 is in contact with a user's skin. The elastomeric portion 27 may provide a soft portion to contact the user's skin which may make the apparatus 1 more comfortable for a user to use.

The elastomeric portion 27 could be made of rubber or any other suitable material.

The apparatus 1 also comprises coupling means 11. The coupling means 11 may comprise any means which may enable the appartaus1 to be coupled to a user. In the examples of FIGS. 2A to 2D the coupling means 11 comprises a strap. The strap could be fastened around a user's wrist, chest or any other suitable part of the user's body. In other examples the coupling means 11 could comprise a necklace or lanyard which could be worn around the user's neck. In some examples the coupling means 11 could comprise an adhesive portion which may enable the apparatus 1 to be adhered to the user's body. In some examples the coupling means could comprise an item of clothing which could be worn by the user.

The apparatus 1 also comprises a damping portion 25. The damping portion 25 is provided between the pulse monitoring module 3 and the coupling means 11. The damping portion 25 comprises an elastomeric material which may be arranged to absorb vibrational energy from the pulse monitoring module 3. The damping portion 25 acts to prevent movement of the pulse monitoring module 3 being transferred to other portions of the apparatus 1. This may act to prevent the apparatus 1 from moving around the user's body when the apparatus 1 is in use. This may also act to protect other components of the apparatus 1. For instance it may prevent any electronic components in other portions of the apparatus 1 from being deformed.

The controlling circuitry 5 controls the apparatus 1 to operate in either a detecting mode of operation or a feedback mode of operation. When the apparatus 1 is in a detecting mode of operation the first piezoelectric transducer 21 is arranged to detect the audio pulse signal and provide an output signal indicative of the detected audio pulse. The output signal is provided to the controlling circuitry 5 so that the controlling circuitry 5 can determine the frequency of the pulse and any other suitable parameters.

When the apparatus 1 is in a feedback mode of operation the controlling circuitry 5 provides a control signal to both the first piezoelectric transducer 21 and the second piezoelectric transducer 22. This causes the deformation of both of the piezoelectric transducers 21, 22. In the example of FIGS. 2A to 2D the piezoelectric transducers are driven in opposing directions so that they move in opposite directions as indicated by the arrows 29. This provides for a larger amplitude of the deformation which may make the haptic feedback easier for a user to sense.

The controlling circuitry 5 drives the piezoelectric transducers 21, 22 with a frequency determined by the frequency, or other suitable parameter, of the detected pulse. In some examples the frequency of the deformations of the piezoelectric transducers 21, 22 may be the same as the frequency of the user's pulse. This enables the user to be provided with information about their pulse without requiring significant cognitive load. As the user is provided with haptic feedback about their pulse they do not need to look at a screen. This could be useful in applications where the user is performing other activities. For instance, if the user is running or performing some other fitness activity or gaming it may be inconvenient or uncomfortable for them to look at a screen to check their heart rate. The haptic feedback enables the user to be provided with the information they need without having to interrupt their fitness or gaming activity. Also as the feedback is provided haptically this does not interrupt other people around the user. For instance, where the user in a public place there is no audio output that may interrupt other people. This also enables the feedback to be kept private and only provided to the user of the apparatus 1.

FIGS. 3A and 3B schematically illustrate cross section of example apparatus 1 according to examples of the disclosure. The example apparatus 1 of FIGS. 3A and 3B also comprises controlling circuitry 5, a pulse detection module 3 and coupling means 11 which may be as described above.

In the example of FIG. 3A the feedback means 9 and the detecting means 7 are provided as the same component. The controlling circuitry 5 acts to control the component to sequentially operate in either a feedback mode of operation or a detecting mode of operation.

In the example of FIG. 3B the feedback means 9 is provided as a separate component to the detecting means 7. The controlling circuitry 5 acts to control the respective components to sequentially operate in either a feedback mode of operation or a detecting mode of operation. The controlling circuitry 5 may act to enable the apparatus 1 to alternate between a feedback mode of operation and a detecting mode of operation.

It is to be appreciated that other arrangements of the apparatus 1 could be used in other examples of the disclosure. For instance, in the above examples the feedback means 9 and the detecting means 7 comprise circular piezoelectric transducers 21, 22. In other examples the piezoelectric transducers 21 could be provided as strips which may be arranged to expand and contract in the different modes of operation.

FIG. 4 illustrates an example method which could be used to control the example apparatus 1. The method could be implemented in any of the example apparatus 1 as described above.

The method comprises, at block 41, controlling a pulse monitoring module 3 so that during a first time period $T_1$ the pulse monitoring module 3 is arranged to detect a user's pulse and, at block 43, controlling the pulse monitoring module 3 so that during a second time period $T_2$ the pulse monitoring module 3 is arranged to provide haptic feedback indicative of the detected pulse.

Block 43 may be implemented immediately after block 41 has been completed. In some examples there may be no time interval between block 41 and block 43. In other examples of the disclosure there may be a small time interval between block 41 and block 43.

Blocks 41 and 43 may last for different durations. As described above, the first time period $T_1$ may be longer than the second time period $T_2$. The first time period $T_1$ may be a lot longer than the second time period $T_2$, for example, the second time period $T_2$ could be within a range of 5 to 50 ms while the first time period $T_1$ could be several seconds. Other ranges could be used in other examples of the disclosure.

Block 41 and 43 may be repeated. In some examples the blocks may be repeated continuously so that as soon as a time period for providing haptic feedback has ended a time period for detecting the pulse begins. The parameters of haptic feedback may correspond to the parameters of the pulse detected in the detecting time period immediately preceding the current feedback time period. This ensures that any delay in the feedback provided to the user is minimised.

FIG. 5 illustrates example controlling circuity 5 which may be provided within the example apparatus 1 as described above. The controlling circuitry 5 illustrated in FIG. 5 may be a chip or a chip-set. The controlling circuitry 5 may provide means for performing the example methods or at least part of the example methods of FIG. 4.

The controlling circuitry 5 comprises processing circuitry 51 and memory circuitry 53. The processing circuitry 51 may be configured to read from and write to the memory circuitry 53. The processing circuitry 51 may comprise one or more processors. The processing circuitry 51 may also comprise an output interface via which data and/or commands are output by the processing circuitry 51 and an input interface via which data and/or commands are input to the processing circuitry 51.

The memory circuitry 53 may be configured to store a computer program 55 comprising computer program instructions (computer program code 67) that controls the operation of the controlling circuitry 5 when loaded into processing circuitry 53. The computer program instructions, of the computer program 55, provide the logic and routines that enable the controlling circuitry 5 to perform the example methods illustrated in FIG. 4 The controlling circuitry 5 by reading the memory circuitry 53 is able to load and execute the computer program 55.

The computer program 55 may arrive at the controlling circuitry 5 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 55. The controlling circuitry 5 may propagate or transmit the computer program 55 as a computer data signal. In some examples the computer program code 57 may be transmitted to the apparatus 1 using a wireless protocol such as Bluetooth, Bluetooth Low Energy, Bluetooth Smart, 6LoWPan (IP$_v$6 over low power personal area networks) ZigBee, ANT+, near field communication (NFC), Radio frequency identification (RFID), wireless local area network (wireless LAN) or any other suitable protocol.

Although the memory circuitry 53 is illustrated as a single component in the figures it is to be appreciated that it may be implemented as one or more separate components some or all of which may be integrated/removable and/or may provide permanent/semi-permanent/dynamic/cached storage.

Although the processing circuitry 51 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

It is to be appreciated that in examples of the disclosure the apparatus 1 may also comprise components which have not been illustrated in the Figures mentioned above. For example the apparatus 1 could comprise transceiver circuitry which may enable information indicative of the user's pulse to be transmitted to another device. The apparatus 1 could also comprise a power source which may be used to power the controlling circuitry and the feedback means 9 and any other suitable components of the apparatus 1.

In some examples the apparatus 1 may be worn by the user so that the user's pulse could be monitored repeatedly for the whole time that the apparatus 1 being worn. This could be useful for health monitoring applications. In such examples the feedback means 9 may be controlled to provide haptic feedback at every interval between detecting time periods. In other examples the feedback means 9 may be controlled so that the haptic feedback is only provided if a parameter of the detected pulse exceeds a threshold. For example the haptic feedback could be provided if the frequency of the user's pulse exceeds a threshold, this may be useful in health applications. In some examples the haptic feedback could be provided if the frequency of the user's pulse falls below a threshold level. This could be used in fitness applications as it could provide an indication to the user to increase the intensity of their activity.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples.

Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
    at least one processor; and
    at least one memory storing instructions, that when executed by the at least one processor, cause the apparatus to at least:
    provide haptic feedback to a user indicative of a detected pulse;
    during a first predetermined time period, detect the pulse of the user and during a second predetermined time period provide haptic feedback indicative of the detected pulse,
    wherein the first predetermined time period is set longer than the second predetermined time period, and
    wherein frequency and amplitude parameters of deformations of the haptic feedback are set to correspond to frequency and amplitude parameters of the pulse of the user detected in a time period immediately preceding a haptic feedback time period;
    deform a portion of the haptic feedback so that the deformation can be perceived via a sense of touch of the user;
    control an amplitude of the deformation using different amplitudes to cause user perception at different activity levels of the user and to cause a frequency of the deformation to be different than a frequency of the detected pulse of the user; and
    based on the user perception at different activity levels of the user, use an acoustic cavity positioned adjacent to at least one piezoelectric transducer, wherein the at least one piezoelectric transducer is driven in opposing directions and configured with a first time period and second time period purpose to change a shape of the portion of the haptic feedback, wherein the first time period and the second time period purpose comprises that during the first time period the at least one piezoelectric transducer acts to detect the pulse of the user and during the second time period the at least one piezoelectric transducer acts to provide a haptic indication of the frequency of the pulse of the user.

2. The apparatus as claimed in claim 1, wherein the second predetermined time period runs sequentially to the first predetermined time period.

3. The apparatus as claimed in claim 1, wherein the apparatus comprises controlling circuitry, detecting circuitry, and feedback circuitry, wherein at least one of the detecting circuitry and the feedback circuitry comprises the at least one piezoelectric transducer.

4. The apparatus as claimed in claim 3, wherein the pulse monitoring circuitry comprises a plurality of transducers and controlling circuitry positioned between two of the plurality of transducers.

5. The apparatus as claimed in claim 3, wherein the pulse monitoring circuitry is provided within a metallic housing wherein the metallic housing provides a bias electrode for a transducer within the pulse monitoring circuitry.

6. The apparatus as claimed in claim 3 comprising an elastomeric portion, wherein the elastomeric portion is positioned within the apparatus so that when the apparatus is worn by the user the elastomeric portion contacts the skin of the user.

7. The apparatus as claimed in claim 3 wherein the acoustic cavity has a size and shape arranged to amplify audio pulse signals from the user.

8. The apparatus as claimed in claim 1, wherein there is no time interval between detecting the pulse of the user and the providing the haptic feedback.

9. The apparatus as claimed in claim 1, wherein the apparatus comprises a flexible substrate.

10. A method comprising:
    controlling pulse monitoring so that, during a first predetermined time period, the pulse monitoring detects a pulse of a user and during a second predetermined time period haptic feedback indicative of the detected pulse is provided;
    controlling the pulse monitoring, so that during a second time period the pulse monitoring provides haptic feedback indicative of the detected pulse,
    wherein the first predetermined time period is set longer than the second predetermined time period,
    wherein frequency and amplitude parameters of deformations of the haptic feedback are set to correspond to frequency and amplitude parameters of the pulse of the user detected in a time period immediately preceding a haptic feedback time period,
    wherein the haptic feedback is configured to deform a portion of the haptic feedback so that the deformation can be perceived via a sense of touch of the user, and
    wherein the haptic feedback is configured to control an amplitude of the deformation using different amplitudes to cause user perception at different activity levels of the user;
    controlling a frequency of the deformation to be different than a frequency of the detected pulse of the user; and
    based on the user perception at different activity levels of the user, use an acoustic cavity positioned adjacent to at least one piezoelectric transducer, wherein the at least one piezoelectric transducer is driven in opposing directions and configured with a first time period and second time period purpose to change a shape of the portion of the haptic feedback, wherein the first time period and the second time period purpose comprises that during the first time period the at least one piezoelectric transducer acts to detect the pulse of the user and during the second time period the at least one piezoelectric transducer acts to provide a haptic indication of the frequency of the pulse of the user.

11. The method according to claim 10, wherein the second predetermined time period runs sequentially to the first predetermined time period.

12. The method according to claim 10 wherein the pulse monitoring comprises detecting an audio signal of the pulse of the user.

13. The method according to claim 12 wherein the detecting the audio signal comprises amplifying the audio signal of the pulse of the user.

14. A non-transitory computer readable medium comprising program instructions stored thereon for performing at least:
  controlling a pulse monitoring so that, during a first predetermined time period, the pulse monitoring detects a pulse of a user;
  controlling the pulse monitoring so that, during a second predetermined time period, the pulse monitoring provides haptic feedback indicative of the detected pulse, wherein frequency and amplitude parameters of deformations of the haptic feedback are set to correspond to frequency and amplitude parameters of the pulse of the user detected in a time period immediately preceding a haptic feedback time period, and
  wherein the haptic feedback is configured to deform a portion of the haptic feedback so that the deformation can be perceived via a sense of touch of the user;
  controlling an amplitude of the deformation using different amplitudes to cause user perception at different activity levels of the user;
  controlling a frequency of the deformation to be different than a frequency of the detected pulse of the user; and
  based on the user perception at different activity levels of the user, use an acoustic cavity positioned adjacent to at least one piezoelectric transducer, wherein the at least one piezoelectric transducer is driven in opposing directions and configured with a first time period and second time period purpose to change a shape of the portion of the haptic feedback, wherein the first time period and the second time period purpose comprises that during the first time period the at least one piezoelectric transducer acts to detect the pulse of the user and during the second time period the at least one piezoelectric transducer acts to provide a haptic indication of the frequency of the pulse of the user.

15. The non-transitory computer readable medium according to claim 14, wherein the second predetermined time period runs sequentially to the first predetermined time period.

16. The non-transitory computer readable medium according to claim 14, wherein the pulse monitoring comprises detecting the audio signal of the-pulse of the user.

17. The non-transitory computer readable medium according to claim 16 wherein the detecting an audio signal comprises amplifying the audio signal of the pulse of the user.

* * * * *